(12) United States Patent
Khan et al.

(10) Patent No.: US 7,501,391 B2
(45) Date of Patent: *Mar. 10, 2009

(54) TREATMENT OF TRANSPLANT SURVIVAL

(75) Inventors: Nisar Ahmed Khan, Rotterdam (NL); Robbert Benner, Barendrecht (NL); Johannes N. M. Yzermans, Rotterdam (NL)

(73) Assignee: Biotempt B.V., Koekange (NL)

( * ) Notice: Subject to any disclaimer, the term of this patent is extended or adjusted under 35 U.S.C. 154(b) by 345 days.

This patent is subject to a terminal disclaimer.

(21) Appl. No.: 10/409,027

(22) Filed: Apr. 8, 2003

(65) Prior Publication Data

US 2003/0219425 A1 Nov. 27, 2003

Related U.S. Application Data

(63) Continuation-in-part of application No. 10/028,075, filed on Dec. 21, 2001.

(51) Int. Cl.
*A61K 38/00* (2006.01)
*A61K 38/04* (2006.01)
*C12N 5/06* (2006.01)
*C12N 5/08* (2006.01)

(52) U.S. Cl. .......................... 514/2; 435/374; 435/375; 530/300; 530/330

(58) Field of Classification Search ........................ None
See application file for complete search history.

(56) References Cited

U.S. PATENT DOCUMENTS

| | | | |
|---|---|---|---|
| 4,427,660 A | 1/1984 | Schiffman et al. | |
| 4,571,336 A | 2/1986 | Houck et al. | |
| 4,753,965 A | 6/1988 | Stemerick et al. | |
| 4,855,285 A | 8/1989 | Stevens | |
| 4,977,244 A | 12/1990 | Muchmore et al. | |
| 5,002,961 A | 3/1991 | Dage et al. | |
| 5,223,397 A * | 6/1993 | Pouletty | 435/7.24 |
| 5,380,668 A | 1/1995 | Herron | |
| 5,677,275 A | 10/1997 | Lunardi-Iskandar et al. | |
| 5,801,193 A * | 9/1998 | Ojo-Amaize et al. | 514/475 |
| 5,851,997 A | 12/1998 | Harris | |
| 5,854,004 A | 12/1998 | Czemilofsky et al. | |
| 5,877,148 A | 3/1999 | Lunardi-Iskandar et al. | |
| 5,942,494 A | 8/1999 | Ginsberg et al. | |
| 5,958,413 A | 9/1999 | Anagnostopulos et al. | |
| 5,968,513 A | 10/1999 | Gallo et al. | |
| 5,972,924 A * | 10/1999 | Keep et al. | 514/183 |
| 5,981,486 A | 11/1999 | Matsushima et al. | |
| 5,994,126 A | 11/1999 | Steinman et al. | |
| 5,997,871 A | 12/1999 | Gallo et al. | |
| 6,051,596 A * | 4/2000 | Badger | 514/409 |
| 6,075,150 A | 6/2000 | Wang et al. | |
| 6,150,500 A | 11/2000 | Salerno | |
| 6,235,281 B1 | 5/2001 | Stenzel et al. | |
| 6,310,041 B1 | 10/2001 | Haddox et al. | |
| 6,319,504 B1 | 11/2001 | Gallo et al. | |
| 6,361,992 B1 | 3/2002 | Szkudlinski et al. | |
| 6,489,296 B1 | 12/2002 | Grinnell et al. | |
| 6,583,109 B1 | 6/2003 | Gallo et al. | |
| 6,596,688 B1 | 7/2003 | Gallo et al. | |
| 6,620,416 B1 | 9/2003 | Gallo et al. | |
| 6,630,138 B2 | 10/2003 | Gerlitz et al. | |
| 6,727,227 B1 | 4/2004 | Khavinson | |
| 6,831,057 B2 | 12/2004 | Baldwin et al. | |
| 6,844,315 B2 | 1/2005 | Khan et al. | |
| 2002/0041871 A1 | 4/2002 | Brudnak | |
| 2002/0064501 A1 | 5/2002 | Khan et al. | |
| 2003/0049273 A1 | 3/2003 | Gallo et al. | |
| 2003/0113733 A1 | 6/2003 | Khan et al. | |
| 2003/0119720 A1 | 6/2003 | Khan et al. | |
| 2003/0148955 A1 | 8/2003 | Pluenneke | |
| 2003/0166556 A1 | 9/2003 | Khan et al. | |
| 2003/0186244 A1 | 10/2003 | Margus et al. | |
| 2003/0215434 A1 | 11/2003 | Khan et al. | |
| 2003/0219425 A1 | 11/2003 | Khan et al. | |
| 2003/0220257 A1 | 11/2003 | Benner et al. | |
| 2003/0220258 A1 | 11/2003 | Benner et al. | |
| 2003/0220259 A1 | 11/2003 | Benner et al. | |
| 2003/0220260 A1 | 11/2003 | Khan et al. | |

(Continued)

FOREIGN PATENT DOCUMENTS

DE 3715662 11/1987

(Continued)

OTHER PUBLICATIONS

Emmel et al, Science, Dec. 22, 1989, vol. 246, pp. 1617-1620.*

(Continued)

*Primary Examiner*—Celine X Qian
*Assistant Examiner*—Jennifer Dunston
(74) *Attorney, Agent, or Firm*—TraskBritt

(57) ABSTRACT

The invention relates to the field of transplantation medicine and to the prevention and treatment of rejection, in particular of chronic rejection, of a transplant by a recipient of the transplant. The invention provides method for modulating transplant survival in a recipient of the transplant comprising providing the transplant with a gene-regulatory peptide or functional analogue thereof. Furthermore, the invention provides use of a gene-regulatory peptide or functional analogue thereof for the production of a pharmaceutical composition for the treatment of a transplant allowing modulating transplant survival in a recipient of the transplant.

5 Claims, No Drawings

U.S. PATENT DOCUMENTS

| | | | |
|---|---|---|---|
| 2003/0220261 | A1 | 11/2003 | Khan et al. |
| 2003/0224995 | A1 | 12/2003 | Khan et al. |
| 2004/0013661 | A1 | 1/2004 | Wensvoort et al. |
| 2004/0208885 | A1 | 10/2004 | Khan et al. |
| 2005/0037430 | A1 | 2/2005 | Khan et al. |
| 2005/0214943 | A1 | 9/2005 | Khan et al. |
| 2005/0227925 | A1 | 10/2005 | Benner et al. |
| 2006/0111292 | A1 | 5/2006 | Khan et al. |
| 2006/0142205 | A1 | 6/2006 | Benner et al. |

FOREIGN PATENT DOCUMENTS

| | | |
|---|---|---|
| DE | 19953339 | 5/2001 |
| EP | 1 300 418 | 4/2003 |
| FR | 2 706 772 | 12/1994 |
| WO | WO 96/04008 | 2/1996 |
| WO | WO 97/49373 | 12/1997 |
| WO | WO 97/49418 | 12/1997 |
| WO | WO 97/49432 | 12/1997 |
| WO | WO 97/49721 | 12/1997 |
| WO | WO 9749432 A1 * | 12/1997 |
| WO | WO 98/35691 | 8/1998 |
| WO | WO 9834631 A1 * | 8/1998 |
| WO | WO 99/59617 | 11/1999 |
| WO | WO 9959617 A2 * | 11/1999 |
| WO | WO 01/10907 A2 | 2/2001 |
| WO | WO 01/11048 A2 | 2/2001 |
| WO | WO 01/29067 | 4/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 03/029292 A2 | 4/2003 |

OTHER PUBLICATIONS

McDonald et al. Interleukin-15 (IL-15) induces NF-kappaB activation and IL-8 production in human neutrophils. Blood. vol. 92, No. 12, pp. 4828-4835, Dec. 1998.*

Oka et al. Immunosuppression in organ transplantation. Japanese Journal of Pharmacology, vol. 71, No. 2, pp. 89-100, Jun. 1996.*

Zhou et al. Transplantation tolerance in NF-kappaB-impaired mice is not due to regulation but is prevented by transgenic expression of Bcl-xL. The Journal of Immunology, vol. 174, No. 6, pp. 3447-3453, Mar. 2005.*

Bradham et al. Activation of nuclear factor-kappaB during orthotopic liver transplantation in rats is protective and does not require Kuppfer cells. Liver Transplantation and Surgery, vol. 5, No. 4, pp. 282-293, Jul. 1999.*

Dietrich et al. Postischemic hypothermia and IL-10 treatment provide long-lasting neuroprotection of CA1 hippocampus following transient global ischemia in rats. Experimental Neurology, vol. 158, pp. 444-450, 1999.*

Le Moine et al. Cold liver ischemia-reperfusion injury critically depends on liver T cells and is improved by donor pretreatment with interleukin 10 in mice. Hepatology, vol. 31, No. 6, pp. 1266-1274, 2000.*

Selzman et al. Interleukin-10 inhibits postinjury tumor necrosis factor-mediated human vascular smooth muscle proliferation. Journal of Surgical Research, vol. 80, pp. 352-356, 1998.*

Engles et al. Exogenous human recombinant interleukin-10 attenuates hindlimb ischemia-reperfusion injury. Journal of Surgical Research, vol. 69, pp. 425-428, 1997.*

Lane et al. Interleukin-10 reduces the systemic inflammatory response in a murine model of intestinal ischemia/reperfusion. Surgery, vol. 122, No. 2, pp. 288-294, 1997.*

Lutterova et al. Marked difference in tumor necrosis factor-alspha expression in warm ischemia- nd cold ischemia-reperfusion of the rat liver. Cryobiology, vol. 41, pp. 301-314, 2000.*

Riera et al. Neutrophils accentuate renal cold ischemia-reperfusion injury. Dose-sependent protective effect of platelet-activating factor receptor antagonist. The Journal of Pharmacology and Experimental Therapeutics, vol. 280, No. 2, pp. 786-794, 1997.*

Donnahoo et al. Early kidney TNF-alpha expression mediates neutrophil infiltration and injury after renal ischemia-reperfusion. American Journal of Physiology, vol. 277, No. 3, Pt. 2, pp. R922-R929, Sep. 1999.*

Daemen et al. Ischemia/reperfusion-induced IFN-gamma up-regulation: involvement of IL-12 and IL-18. The Journal of Immunology, vol. 162, pp. 5506-5510, 1999.*

Connelly et al., Biphasic Regulation of NF-kB Activity Underlies the Pro- and Anti-inflammatory Actions of Nitric Oxide, The Journal of Immunology, 2001, pp. 3873-3881, 166, The American Association of Immunologists, USA.

Friedlander, Tackling anthrax, Nature, Nov. 8, 2001, pp. 160-161, vol. 414.

Iskandar et al., "Effects of a urinary factor from women in early pregnancy on HIV-a, SIV and associated disease," Nature Medicine, Apr. 1998, vol. 4, No. 4, pp. 428-434.

Lang et al., "Induction of apoptosis in Kaposi's sarcoma spindle cell cultures by the subunits of human chorionic gonadtropin," AIDS 1997, vol. 11, No. 11, pp. 1333-1340.

Medzhitov, Toll-like Receptors and Innate Immunity, Nature Reviews/Immunology, Nov. 2001, pp. 135-145, vol. 1.

PCT International Search Report, PCT/NL01/00259, dated Dec. 18, 2001, 3 pages.

PCT International Preliminary Examination Report, PCT/NI99/00313, dated Jul. 21, 2000, 6 pages.

PCT International Search Report, PCT/EP99/00313, dated Nov. 29, 1999, 3 pages.

International Search Report, International Application No. PCT/NL02/00639, mailed Aug. 4, 2003 (8 pages).

Christman et al., Nuclear factor kappaB: a pivotal role in the systemic inflammatory response syndrome and new target for therapy, Intens Care Med, 1998, pp. 1131-1138, vol. 24.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kanungo et al., Advanced Maturation of Heteropneustes Fossilis (Bloch) by Oral Administration of Human Chorionic Gonadotropin, J. Adv. Zool., 1999, pp. 1-5, vol. 20.

Patil, A., et al., "The Study of the Effect of Human Chorionic Gonadotrophic (HCG) Hormone on the Survival of Adrenal Medulla Transplant in Brain. Preliminary Study," 87 Acta Neurochir (WIEN) 76-78 (1987).

Rohrig et al., Growth-stimulating Influence of Human Chorionic Gonadotropin (hCG) on Plasmodium falciparum in vitro, Zentralblatt Bakt, 1999, pp. 89-99, vol. 289.

Slater, Lewis M., et al., "Decreased Mortality of Murine Graft-Versus-Host Disease by Human Chorionic gonadotropin,"23(1) Transplantation 103-104 (Jan. 1977).

Tak et al., NF-kappaB: a key role in inflammatory diseases, J Clin Invest., 2001, pp. 7-11, vol. 107.

Tan et al., The role of activation of nuclear factor-kappa B of rat brain in the pathogenesis of experimental allergic encephalomyelitis, Acta Physiol Sinica, 2003, pp. 58-64, vol. 55.

Tovey et al., Mucosal Cytokine Therapy: Marked Antiviral and Antitumor Activity, J. Interferon Cytokine Res., 1999, pp. 911-921, vol. 19.

Albini, A., et al., "Old drugs as novel angiogenesis inhibitors: Preclinical studies with NAC, hCG, EGCG and somatostatin," 17 Clinical & Experimental Metastasis 739 (1999).

Blackwell, Timothy S., et al., "The Role of Nuclear Factor-kB in Cytokine Gene Regulation," 17 Am. J. Respir. Cell Mol. Biol. 3-9 (1997).

Keller, S., et al., "Human Chorionic Gonadotropin (hCG) Is a Potent Angiogenic Factor for Uterine Endothelial Cells in Vitro," 20(5-6) Placenta, p. A37 (Jul. 1999).

Khan, Nisar A., et al., "Inhibition of Diabetes in NOD Mice by Human Pregnancy Factor," 62(12) Human Immunology 1315-1323 ( Dec. 2001).

Khan, Nisar A., et al., "Inhibition of Septic Shock in Mice by an Oligopeptide From the β-Chain of Human Chorionic Gonadotrophin Hormone," 63(1) Human Immunology 1-7 (Jan. 2002).

Muchmore et al., Immunoregulatory Properties of Fractions from Human Pregnancy Urine: Evidence that Human Chorionic Gonadotropin is not Responsible. The Journal of Immunology, Mar. 1997, pp. 881-886, vol. 118, No. 3.

Muchmore et al., Purification and Characterization of a Mannose-Containing Disaccharide Obtained from Human Pregnancy Urine, Journal of Experimental Medicine, Dec. 1984, pp. 1672-1685, vol. 160.

Wulczyn, F. Gregory, et al., "The NF-kB/Rel and IkB gene families: mediators and immune response and inflammation," 74(12) J. Mol. Med. 749-769 (1996).

Yamamoto, Y., et al., "Role of the NF-kB Pathway in the Pathogenesis of Human Disease States," 1(3) Current Molecular Medicine 287-296 (Jul. 2001).

Samaniego et al., Induction of Programmed Cell Death in Kaposi's Sarcoma Cells by Preparations of Human Chorionic Gonadotropin, Journal of the National Cancer Institute, Jan. 20, 1999, pp. 135-143, vol. 91, No. 2.

PCT International Search Report, PCT/EP2005/003707, dated Jul. 5, 2005.

Abraham, E., "Coagulation Abnormalities in Acute Lung Injury and Sepsis," Am. J. Respir. Cell Mol. Biol., 2000, pp. 401-404, vol. 22.

Adib-Conquy et al., "NF-kappaB Expression in Mononuclear Cells in Patients with Sepsis Resembles That Observed in Lipopolysaccharide Tolerance," Am. J. Respir. Crit. Care Med., 2000, pp. 1877-1883, vol. 162.

Arima et al., "IL-2-Induced Growth of CD8+ T Cell Prolymphocytic Leukemia Cells Mediated by NF-kappaB Induction and IL-2 Receptor alpha Expression," Leukemia Research, 1998, pp. 265-273, vol. 22, No. 3.

Baeuerle et al., "Function and Activation of NF-kappaB in the Immune System," Annu. Rev. Immunol., 1994, pp. 141-179, vol. 12.

Bethea et al., "Traumatic Spinal Cord Injury Induces Nuclear Factor-kappaB Activation," The Journal of Neuroscience, May 1, 1998, pp. 3251-3260, vol. 18, No. 9.

Bodfish et al., "Treating the Core Features of Autism: Are We There Yet?" Mental Retardation and Developmental Disabilities Research Reviews, 2004, pp. 318-326, vol. 10.

Brown et al., "Two Forms of NF-kappaB1 (p105/p50) in Murine Macrophages: Differential Regulation by Lipopolysaccharide, Interleukin-2, and Interferon-gamma," Journal of Interferon and Cytokine Research, 1997, pp. 295-306, vol. 17.

Emmel et al., "Cyclosporin A Specifically Inhibits Function of Nuclear Proteins Involved in T Cell Activation," Science, Dec. 22, 1989, pp. 1617-1620, vol. 246.

Epinat et al., "Diverse agents act at multiple levels to inhibit the Rel/NF-kappaB signal transduction pathway," Oncogene, 1999, pp. 6896-6909, vol. 18.

Faust et al., "Disseminated intravascular coagulation and purpura fulminans secondary to infection," Bailliere's Clinical Haematology, 2000, 179-197, vol. 13. No. 2.

Jimenez-Garza et al., "Early Effects of Modulating Nuclear factor-kappaB Activation on Traumatic Spinal Cord Injury in Rats," Ann. N.Y Acad. Sci., 2005, pp. 148-150, vol. 1053.

Kidd et al., "Autism, An Extreme Challenge to Integrative Medicine. Part II: Medical Management," Alternative Medicine Review, 2002, pp. 472-499, vol. 7, No. 6.

Kronfol et al., "Cytokines and the Brain: Implications for Clinical Psychiatry," Am. J. Psychiatry, May 2000, pp. 683-694, vol. 157, No. 5.

Li et al., "NF-kappaB Regulation in the Immune System," Nature Reviews/Immunology, Oct. 2002, pp. 725-734, Vol. 2.

Malek-Ahmadi, P., "Role of Cytokines in Psychopathology: Therapeutic Implications," Drug News Prospects, Jun. 1998, pp. 271-276, vol. 11, No. 5.

McBean et al., "Rodent Models of Global Cerebral Ischemia: A Comparison of Two-Vessel Occlusion and Four-Vessel Occlusion," Gen. Pharmac., 1998, pp. 431-434, vol. 30, No. 4.

Neely et al., "Then and now: Studies using a burned mouse model reflect trends in burn research over the past 25 years," Burns, 1999, pp. 603-609, vol. 25.

Smith et al., "Recent developments in drug therapy for multiple sclerosis," Multiple Sclerosis, 1999, pp. 110-120, vol. 5.

Traystman, R., "Animal Models of Focal and Global Cerebral Ischemia," ILAR Journal, 2003, pp. 85-95, vol. 44, No. 2.

Weinberger et al., "Mechanisms Mediating the Biologic Activity of Synthetic Proline, Glycine, and Hydroxyproline Polypeptides in Human Neurophils," Mediators of Inflammation, 2005, pp. 31-38, vol. 1.

Yang et al., "Increased cortical nuclear factor kappaB (NF-kappaB) DNA binding activity after traumatic brain injury in rats," Neuroscience Letters, 1995, pp. 101-104, vol. 197.

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Ivanov et al., "Hemoglobin as a Source of Endogenous Bioactive Peptides: The Concept of Tissue-Specific Peptide Pool," Biopolymers, 1997, pp. 171-188, vol. 39.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Morozov et al., "Natural and Synthetic Thymic Peptides as Therapeutics for Immune Dysfunction," Int. J. Immunopharmac., 1997, pp. 501-505, vol. 19, No. 9/10.

Cui et al., Am. J. Physiol. Integr. Comp. Physiol., 2004, pp. R699-R709, vol. 286.

Dwinnell et al., Atlas of Diseases of the Kidney, Blackwell Sciences, 1999, pp. 12.1-12.12, Ch. 12.

Kalns et al., Biochem. Biophys. Res. Comm., 2002, pp. 506-509, vol. 297.

Kalns et al., Biochem. Biophys. Res. Comm., 2002, pp. 41-44, vol. 292.

Merck Index, 17th ed. 1999, pp. 1145-1146, 1841-1848, 2539, 2551.

Merriam-Webster Medical Dictionary, 1994, p. 82.

Moayeri et al., Journal of Clinical Investigation, Sep. 2003, pp. 670-682, vol. 112, No. 5.

Ngo et al., The protein folding problem and tertiary structure prediction, 1994, pp. 492-494.

Pellizzari et al., FEBS Letters, 1999, pp. 199-204, vol. 462.

* cited by examiner

SEQUENCE LISTING

```
<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Gln Gly Val
 1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gln Gly Val
 1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gln Gly Ala
 1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Pro Ala Leu Pro
 1               5

<210> SEQ ID NO 5
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Pro Ala Leu Pro
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ala Pro Ala Leu Pro
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Pro Ala Leu Pro Gln
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Pro Ala Ala Pro Gln
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Pro Ala Leu Ala Gln
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ala Gly Val
  1
```

-continued

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Leu Ala Ala Leu Pro
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Pro Ala Leu Ala
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Leu Pro Ala Leu Pro Gln
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Leu Ala Ala Leu Pro Gln
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Leu Pro Ala Leu Pro Ala
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Gly Val Leu Pro Ala Leu Pro
 1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gln Gly Val Leu Pro Ala Leu Pro Gln Val Val Cys
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Gly Cys Pro Arg Gly Val Asn Pro Val Val Ser
 1               5                  10

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Gly Cys
 1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Thr Arg Val
 1

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Pro Ala Leu Pro Gln Val Val Cys
 1               5                  10

<210> SEQ ID NO 22

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gln Gly Val Leu Pro Ala Leu Pro Gln
 1               5                  10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Leu Pro Ala Leu Pro Gln
 1               5

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Val Cys Asn Tyr Arg Asp Val Arg Phe Glu Ser Ile Arg Leu Pro
 1               5                  10                  15

Gly Cys Pro Arg Gly Val Asn Pro Val Val Ser Tyr Ala Val Ala Leu
                20                  25                  30

Ser Cys Gln Cys Ala Leu
        35

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Arg Cys Arg Pro Ile Asn Ala Thr Leu Ala Val Glu Lys Glu
 1               5                  10                  15

Gly Cys Pro Val Cys Ile Thr Val Asn Thr Thr Ile Cys Ala Gly Tyr
                20                  25                  30

Cys Pro Thr
        35

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Lys Ala Pro Pro Pro Ser Leu Pro Ser Pro Ser Arg Leu Pro Gly
 1               5                  10                  15
```

```
Pro Ser

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ile Arg Leu Pro Gly Cys Pro Arg Gly Val Asn Pro Val Val Ser
  1               5                  10                  15

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
agctcagagg gggactttcc gagag                                           25

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Val Val Cys
  1
```

TREATMENT OF TRANSPLANT SURVIVAL

CROSS REFERENCE TO RELATED APPLICATION

This application is a continuation-in-part of U.S. patent application Ser. No. 10/028,075, filed Dec. 21, 2001, pending, the content of the entirety of which is incorporated by this reference.

TECHNICAL FIELD

The current invention relates to biotechnology generally, and more particularly to the body's innate way of modulation of important physiological processes and builds on insights reported in PCT International Publication WO99/59617, PCT International Publication WO01/00259 and PCT International Application PCT/NL02/00639, the contents of all of which are incorporated by this reference.

BACKGROUND

In these aforementioned applications, small gene-regulatory peptides are described that are present naturally in pregnant women and are derived from proteolytic breakdown of placental gonadotropins such as human chorionic gonadotropin (hCG) produced during pregnancy. These peptides (in their active state often only at about 4 to 6 amino acids long) were shown to have unsurpassed immunological activity that they exert by regulating expression of genes encoding inflammatory mediators such as cytokines. Surprisingly, it was found that breakdown of hCG provides a cascade of peptides that help maintain a pregnant woman's immunological homeostasis. These peptides are nature's own substances that balance the immune system to assure that the mother stays immunologically sound while her fetus does not get prematurely rejected during pregnancy but instead is safely carried through its time of birth.

Where it was generally thought that the smallest breakdown products of proteins have no specific biological function on their own (except to serve as antigen for the immune system), it now emerges that the body in fact routinely utilizes the normal process of proteolytic breakdown of the proteins it produces to generate important gene-regulatory compounds, short peptides that control the expression of the body's own genes. Apparently the body uses a gene-control system ruled by small broken down products of the exact proteins that are encoded by its own genes.

It has been long known that during pregnancy the maternal system introduces a status of temporary immunomodulation which results in suppression of maternal rejection responses directed against the fetus. Paradoxically, during pregnancy, often the mother's resistance to infection is increased and she is found to be better protected against the clinical symptoms of various auto-immune diseases such as rheumatism and multiple sclerosis. The protection of the fetus can thus not be interpreted only as a result of immune suppression. Each of the above three applications have provided insights by which the immunological balance between protection of the mother and protection of the fetus can be understood.

It was shown that certain short breakdown products of hCG (i.e., short peptides which can easily be synthesized, if needed modified, and used as pharmaceutical composition) exert a major regulatory activity on pro- or anti-inflammatory cytokine cascades that are governed by a family of crucial transcription factors, the NFκB family which stands central in regulating the expression of genes that shape the body's immune response.

Most of the hCG produced during pregnancy is produced by cells of the placenta, the exact organ where cells and tissues of mother and child most intensely meet and where immuno-modulation is most needed to fight off rejection. Being produced locally, the gene-regulatory peptides which are broken down from hCG in the placenta immediately balance the pro- or anti-inflammatory cytokine cascades found in the no-mans land between mother and child. Being produced by the typical placental cell, the trophoblast, the peptides traverse extracellular space; enter cells of the immune system and exert their immuno-modulatory activity by modulating NFκB-mediated expression of cytokine genes, thereby keeping the immunological responses in the placenta at bay.

BRIEF SUMMARY OF THE INVENTION

It is herein postulated that the beneficial effects seen on the occurrence and severity of auto-immune disease in the pregnant woman result from an overspill of the hCG-derived peptides into the body as a whole; however, these effects must not be overestimated, as it is easily understood that the further away from the placenta, the less immuno-modulatory activity aimed at preventing rejection of the fetus will be seen, if only because of a dilution of the placenta-produced peptides throughout the body as a whole. However, the immuno-modulatory and gene-regulatory activity of the peptides should by no means only be thought to occur during pregnancy and in the placenta; man and women alike produce hCG, for example in their pituitaries, and nature certainly utilizes the gene-regulatory activities of peptides in a larger whole.

Consequently, a novel therapeutic inroad is provided, using the pharmaceutical potential of gene-regulatory peptides and derivatives thereof. Indeed, evidence of specific up- or down-regulation of NFκB driven pro- or anti-inflammatory cytokine cascades that are each, and in concert, directing the body's immune response was found in silico in gene-arrays by expression profiling studies, in vitro after treatment of immune cells and in vivo in experimental animals treated with gene-regulatory peptides. Also, considering that NFκB is a primary effector of disease (A. S. Baldwin, J. Clin. Invest., 2001, 107:3-6), using the hCG derived gene-regulatory peptides offer significant potential for the treatment of a variety of human and animal diseases, thereby tapping the pharmaceutical potential of the exact substances that help balance the mother's immune system such that her pregnancy is safely maintained.

DETAILED DESCRIPTION OF THE INVENTION

The invention in particular relates to the field of transplantation medicine and to the prevention and treatment of rejection, in particular of chronic rejection, of a transplant by a recipient of the transplant. Chronic rejection (CR)—also termed chronic allograft dysfunction (CAD)—of solid organ allografts or transplants, regardless of type, develops slowly over a period of months or years. The process is characterized by luminal narrowing and occlusion of arteries and arterioles secondary to the proliferation of intimal smooth-muscle cells. These cells express receptors for several growth factors, such as epidermal growth factor, insulin-like growth factor-1, PDGF-α and PDGF-β. Endothelial cells and monocytes/macrophages in the vessel wall also produce fibrosis-inducing factors, including TGF-β, IL-1 and IL-6. Interstitial fibrosis becomes prominent during chronic rejection.

The mechanisms of acute and chronic rejection in transplantation have gradually been clarified during the past 40 years. Several studies have shown that episodes of acute rejection—particularly severe, recurrent, and late episodes of rejection—are major risk factors for chronic rejection.

Various non-immunologic factors have been found to be important contributors as well. Because it has become apparent that multiple factors play a part in chronic rejection, the more inclusive term "chronic allograftopathy" has been introduced. Chronic allograftopathy is manifested clinically by a gradual decrease in function of the transplanted organ, for kidneys for example manifested as kidney failure preceded by hypertension and low-grade proteinuria, usually occurring months or years after transplantation. Characteristic histopathological features include obliterative intimal fibrosis in the arteries of the graft (transplant arteriopathy), widespread duplication of the glomerular basement membrane (chronic transplant glomerulopathy), tubular atrophy, and interstitial fibrosis.

Not uncommonly, however, only interstitial fibrosis and endothelial (tubular) atrophy are present in biopsies of the allograft.

Chronic rejection is a process that keeps organ transplantation from being more than a relatively short-term treatment of life-time diseases. The rate of attrition of allografts secondarily to chronic rejection has not changed substantially despite improvement in one-year graft survival. Currently, no tests can predict the development of the process and no drugs can control or reverse it. Clinical management of transplant recipients—incorporating both immunologically based and non-immunologically based intervention strategies—aimed at minimizing initial risk factors towards the progression of chronic rejection may improve long-term allograft survival. In the absence of specific treatment, avoidance or modulation of risk factors may reduce the rate of progression.

At least two hypotheses have been suggested to explain the etiology of chronic rejection: the first is that the phenomenon is primarily an alloantigen-dependent event influenced by early acute immunological injury to the graft and by later ongoing host alloresponsiveness; the second is that donor-associated antigen-independent factors and those surrounding the engraftment procedure influence the chronic changes. Major alloantigen-dependent events comprise for example HLA (human leukocyte antigen) mismatching. Antigenic differences with the donor increase alloresponsiveness of the host to the transplanted organ. In multicenter analyses, every HLA mismatch produces a 5% decline in long-term graft survival; a complete mismatch has a projected 20-year survival rate of 13%. Early, acute, reversible rejection appears to be the most important antigen-dependent risk factor for chronic rejection, particularly episodes of acute rejection occurring after the first three months. It is likely but still uncertain that, as the incidence of acute rejection declines with more effective immunosuppression, the incidence of chronic rejection will also decrease.

However, non-immunologic risk factors (alloantigen-independent events) for chronic rejection have gained increasing attention. Although some antigen-independent events such as prolonged cold ischemia may be preventable by not shipping the transplants and transplanting the allograft immediately after it has been taken out of the donor, most non-specific donor-associated factors are not—particularly in the current era of critical organ donor shortage. In fact, attempts to increase numbers of organs from marginal donors are underway. These include the use of kidneys from older, hypertensive or diabetic sources as well as from non-heart-beating donors. However, little information as to the actual state of such kidneys and their long-term results is available. This is important because increasing numbers of patients are likely to receive "high risk" kidneys.

For example, the policy of giving priority to potential recipients of cadaveric allografts who are matched with the donor at all six HLA loci (henceforth referred to as HLA-matched) has been in place since 1990 and is supported by a repeatedly demonstrated survival advantage. However, by sheer necessity, matching of transplants between transplantation centers and thus sharing of organs from regionally or nationally widely apart areas or countries necessitates time-consuming shipment of the transplant and prolongs the duration of cold ischemia, the time that the transplant is in between donor and recipient and does not receive the necessary nutrients and oxygen. This severely affects the survival of the graft. It was for example found that shipment of cadaveric renal allografts between organ-procurement organizations affects allograft survival. Indeed, Takemoto et al. (N Eng J Med, 327:834-839, 1992; N Eng J Med, 343:1078-1084, 2000) reported that HLA-matched renal allografts have an estimated half-life of 12.4 years, as compared with an estimated half-life of 8.6 years for HLA-mismatched allografts. They suggested that the decreased frequency of acute rejection explained this difference. Held et al. (N Eng J Med, 331:765-770, 1994) found that the survival of renal allografts with no HLA mismatches was longer than that of allografts with any degree of HLA mismatching; the risk of allograft failure increased by 6 percent for every increase in the number of HLA mismatches. Held et al. also reported that the adjusted risk of allograft failure increases by 8 percent for every 12 hours of cold ischemia and concluded that the actual benefit of HLA matching would be small, because of the attendant increases in the duration of cold ischemia and its relation with decreased allograft survival. Mange et al. (N Eng J Med, 345: 1237-1242, 2001) for example found a significantly higher rate of allograft failure (17 percent) within the first year among recipients of shipped allografts with HLA mismatches, an effect that can be explained by the longer duration of cold ischemia and by more frequent loss of allografts in the first year as a result of acute rejection. These findings show that not only the degree of HLA mismatching but also the duration of cold ischemia are important determinants of the survival of shipped allografts, but the effect of one offsets the effect of the other. HLA-mismatched allografts also had a higher rate of acute rejection leading to the loss of the allograft in the first year. These findings are similar to findings in animal models, in which a prolonged duration of cold ischemia increased the severity of the immune response to the transplanted organ.

A critical alloantigen-independent risk factor in chronic graft dysfunction is ischemia-reperfusion injury of the transplant, for example occurring during and after organ retrieval, storage shipment and transplantation. Brain death is a condition of the donor that also may affect both early and long-term results of transplantation. The effects of this central catastrophe on physiological and structural derangements in the peripheral organs are becoming defined.

Cardiac arrhythmias, myocardial ischemia and myocyte necrosis are common, resulting in insufficient blood supply to the more peripheral organs and tissues, among which the prospective transplant. Changes in the lungs include pulmonary edema, capillary damage and diffuse interstitial and intra-alveolar hemorrhage. There are increasing data on the expression of inflammatory mediators in peripheral organs from brain dead donors, which induce a more intense and accelerated recipient response than those from anesthetized living controls. Also a feature of brain death, ischemia-reperfusion injury of solid organ allografts is associated with an increased risk of primary nonfunction, delayed graft function, acute rejection and chronic reaction. Both initial ischemia and subsequent reperfusion contribute to the injury.

Anaerobic metabolism with cessation of blood flow produces loss of energy dependent transmembrane ion transport and ATP depletion. Tissue swelling from accumulating intracellular fluid and electrolytes following reperfusion obstructs capillary flow and increases intravascular viscosity. A series of inflammatory mediators are elaborated, particularly reactive oxygen intermediates. Nuclear factor-κB (NFκB) is critical for the transcription of multiple genes involved in ischemia-reperfusion injury. Clinical and experimental studies have shown that ischemia-reperfusion injury not only results in activation of the TLRs and the complement system through both the classical and the alternative pathway, but also in increase pro-inflammatory cytokine release. Because of rapid cytokine expression in the injured tissue, polymorphonuclear leukocytes enter within hours and trigger subsequent inflammatory events. Upregulation of HLA (MHC) expression further increases graft immunogenicity, especially in HLA-mismatched cases. Expression of cytokines, chemokines, adhesion molecules and fibrogenic growth factors is again increased, and $CD4^+$ T lymphocytes and monocytes/macrophages infiltrate in large numbers within three to four days. The role of T lymphocytes in ischemia-reperfusion injury is also important. Adoptive transfer studies and anti-CD4 monoclonal antibody therapy were employed in a T cell deficient mouse model to examine the mechanisms of ischemia-reperfusion injury to the liver. The data suggested that $CD4^+$ T lymphocytes are further mediators of the resultant subacute inflammatory response. Both the CD28-B7 and CD40-CD40T cell costimulatory activation may also be important in an alloantigen-independent setting.

Currently, only optimal selection and treatment of donors before the recovery of the organ, shortening the duration of cold ischemia, and the preferential use of living donors (related or unrelated) appear to be the most practical and important ways to ensure that a transplanted organ or tissue is protected from acute peritransplantational injuries. Recent data have established that the use of for example kidneys from poorly matched, living unrelated donors leads to long-term results equivalent to those achieved among recipients of kidneys from haploidentical, living related donors or of uncompromised cadaveric grafts with zero HLA mismatches. Despite the well-known beneficial effect of complete HLA matching in cadaveric organ transplantation, this recent experience emphasizes the importance of the quality of the allograft, which outweighs the effect of partial HLA matching. As the upregulation of cytokines, adhesion molecules and chemokines appear to influence early and late results of transplantation strategies to normalize initial changes will be valuable in clinical transplantation.

The invention provides a method for modulating transplant survival, in particular of increasing transplant survival by avoiding or reducing the risk on acute or chronic rejection in a recipient of the transplant comprising providing the transplant with a signaling molecule comprising a peptide, in particular a short, gene regulatory peptide as provided herein or a functional analogue thereof. It is preferred that the gene regulatory activity of the signaling molecule comprises the modulation of translocation and/or activity of a gene transcription factor. In a preferred embodiment, the gene transcription factor comprises an NF-κB/Rel protein, and to increase transplant survival, it is preferred that translocation and/or activity of the NF-κB/Rel protein is modulated such that ischemia-reperfusion injury of the transplant is reduced. Use of an NF-κB regulating peptide, as provided herein, is in particular provided. Regulating NF<κB expression in the transplant allows for modulating the ischemia-reperfusion damage inflicted upon the transplant in the transplantation process. This treatment reduces in one aspect of the invention the acute, ischemia-induced increase in antigenicity of a transplant, causing less risk on acute rejections.

In another aspect this treatment reduces ischemia-reperfusion injury induced inflammation in the transplant, with the end-result that the chances on the occurrence of chronic rejection are decreased and transplant survival is greatly increased. A gene regulatory peptide can for example be derived from breakdown products of a chorionic gonadotropin (CG) such as human chorionic gonadotropin (hCG), and can easily be synthesized according to the known amino acid sequences derived from the CG sequence, as is for example shown in WO 01/72831. It is preferred that the peptide is selected from the group of peptides LQG, AQG, LQGV (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), LQGVLPALPQVVC (SEQ ID NO: 17), LPGCPRGVNPVVS (SEQ ID NO: 18), LPGC (SEQ ID NO: 19), MTRV (SEQ ID NO: 20), MTR, VVC.

The invention provides a method for modulating transplant survival in a recipient of the transplant comprising providing the transplant with a signaling molecule comprising a peptide, in particular a short, gene regulatory peptide as provided herein or a functional analogue thereof. It is preferred that the gene regulatory activity of the signaling molecule comprises the modulation of translocation and/or activity of a gene transcription factor. In a preferred embodiment, the gene transcription factor comprises an NF-κB/Rel protein or another transcription factor involved in the production of pro-inflammatory cytokines such as AP-1. These short, gene regulatory peptides are commonly from 2 to 15 amino acids long, but preferably shorter, e.g., from 3 to 12 amino acids, i.e., 4, 5, 6 or 7 amino acids long and are derivable by proteolytic breakdown of endogenous proteins of an organism, or are derivable by proteolytic breakdown of proteins of a pathogen, i.e., during the presence of the pathogen in a host organism, and act as a signaling molecule to cells of the organism, in that they can exert an often very specific gene regulatory activity on cells of the organism. In a particular embodiment, the invention provides specific signaling molecules and mechanisms allowing for therapeutically controlling for example NFκB-initiated or AP-1 initiated gene expression, and thereby modulating pro- and anti-inflammatory cytokine expression in a transplant.

In one example of the invention the donor of a transplant is provided with the signaling molecule by perfusing the donor with a perfusion fluid comprising a gene-regulatory peptide selected from the group of peptides LQG, AQG, LQGV (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), LQGVLPALPQVVC (SEQ ID NO: 17), LPGCPRGVNPVVS (SEQ ID NO: 18), LPGC (SEQ ID NO: 19), MTRV (SEQ ID NO: 20), MTR, VVC. Such a perfusion fluid is herein also provided, basis for such a perfusion fluid can be an isotonic saline solution or a phosphate buffered salt solution to which one, or a mixture, of several of the above peptides is added. Preferred peptide concentrations to use lay within the range of 1 to 1000 mg/l. It is of course also possible to provide the peptide in a more concentrated bolus injection. To further improve the perfusion fluid, one may add substances such as ATP, adenosine or ribose, glucose, free amino acids such as glycine, insulin, and so on. An example of such an improved perfusion fluid is given in table 1.

The invention also provides a hypertonic pharmaceutical composition, such as a perfusion fluid or a transplant preservation fluid comprising a NF-κB down-regulating peptide or functional analogue thereof. For example, when the donor is brain dead, it is herein provided to use a hypertonic perfusion fluid, such as a hypertonic salt solution provided with one or more of the herein mentioned NFκB regulatory peptides at a concentration of 1 to 1000 mg/l. Administration of hypertonic saline (HS) with gene-regulatory peptide to the brain death donor intravenously causes an initial rapid fluid influx into the vasculature. This is due to the sudden hypertonic state of plasma caused by the infusion of HS (for example 7.5%, 1283 mmol/l NaCl) in a relatively short time. Other useful sodium concentrations range from 1.2% to 10%. Water is shifted from the intracellular spaces, first the erythrocytes and endothelial cells and then from the tissue cells, into the extracellular compartment. Shrinkage of the endothelium has also beneficial microcirculatory effects due to the reduced resistance of the capillaries. Interstitial water also moves into the intravascular compartment by the osmotic gradient. Hypertonic saline expands intravascular volume by mobilising fluid that is already present in the body; intracellular and interstitial fluid is shifted into the intravascular space. Plasma volume expansion is therefore achieved with less free water administration than with isotonic plasma expanders. The effect of HS on plasma volume is transient since the fluid will shift from the intravascular space back to the extravascular space. Other useful hypertonic solutions may be prepared as well: such as hypertonic NaCl (2400 mosM), hypertonic glucose (2400 mosM), hypertonic sorbitol (2400 mosM), hypertonic glucose (1200 mosM)/glycine (1200 mosM), hypertonic glucose (600 mosM)/mannitol (600 mosM)/glycine (1200 mosM), and hypertonic sorbitol (1200 mosM)/glycine (1200 mosM), each provided with gene-regulatory peptide at 1 to 1000 mg/l. In particular, it is herein provided to use these hypertonic solutions with gene-regulatory peptide initially as a small volume (4-5 ml/kg) infusion fluid. An 80-kg man should receive for example 320-400 ml hypertonic solution with 1-5 mg peptide or functional equivalent/kg body weight. Taking into account an average blood volume of 6 L (6000 ml) and a hematocrit of 45%, the small volume of HS will be distributed into approximately 3300 ml cellular free blood volume. This corresponds to an increase of the cellular free volume of approximately 3620-3700 ml. This also corresponds to approximately 9-11% plasma volume replacement. Initially, for every ml of hypertonic solution with gene regulatory peptide infused, about 7 ml of free water is drawn into the blood stream. Then, once the peptide is distributed and equilibrium is reached, an additional 2240-2800 ml free water will be available in the vascular system. This will cause an expansion of the cellular free blood volume, which will reach about 5860-6500 ml. Thus, under equilibrium conditions, approximately 5-6% of the plasma volume will be replaced by hypertonic solution with gene-regulatory peptide. Then, reperfusion of the donor can be continued with normal (i.e., isotonic) reperfusion fluid, such as Ringer's lactate, or even hypotonic solutions of for example hypotonic saline. This results in an expansion of intracellular volume, further facilitating entry of gene-regulatory peptide.

In another example of the invention the transplant organ is provided with the signaling molecule by removing the transplant from its donor and providing the transplant only after it has been taken out of the donor with a gene-regulatory peptide selected from the group of peptides LQG, AQG, LQGV (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), LQGVLPALPQVVC (SEQ ID NO: 17), LPGCPRGVNPVVS (SEQ ID NO: 18), LPGC (SEQ ID NO: 19), MTRV (SEQ ID NO: 20), MTR, VVC.

Providing the transplant with a gene-regulatory peptide can for example be done by immersing the transplant in a preservation fluid, basis for such a fluid can be an isotonic saline solution or a phosphate buffered salt solution or a Ringer's lactate solution to which one, or a mixture, of several of the above peptides is added. Preferred peptide concentrations to use lay within the range of 1 to 1000 mg/l. It is of course also possible to provide the peptide in a more concentrated bolus injection, or to perfuse the transplant with a perfusion fluid as provided above.

Especially in conditions wherein the donor is cadaveric, it is preferred to provide the transplant with gene-regulatory peptide only when taken out of the donor, and preferably prior to the placement of the transplant in its recipient. The invention also provides a method for modulating transplant survival in a recipient further comprising treating the recipient with a pharmaceutical composition, such as a composition for reducing the risk of transplant rejection. It is herein for example provided to treat a recipient of a transplant that is already treated with a gene-regulatory peptide according to the invention with an immunosuppressive agent such as azathioprine which results in a blockade of purine synthesis (by DNA and RNA inhibitions) in bone marrow myclocytes and in leukocytes, or with antilymphocyte antibodies to cause opsonization of lymphocytes, clearance of lymphocytes, or both and cause lysis of lymphocytes directed against the transplant, or to treat the recipient with cyclosporine to cause inhibition of interleukin-2 synthesis by means of calcineurin blockade in T cells and to stimulate TGF-β production in various cells, or to treat with a anti-CD3 (OKT3) monoclonal antibody that binds to the CD3 molecular complex on T-cells, to opsonize and sequester the cells and modulate the T-cell receptor, or to treat with tacrolimus to inhibit interleukin-2 synthesis by means of calcineurin blockade in T cells, or to treat with mycophenolate mofetil, resulting in a blockade of the de novo pathway of purine synthesis by inhibition of the enzyme IMPDH, or to treat with sirolimus, thereby inhibiting interleukin-2-mediated signal transduction and causing cell-cycle progression and cell proliferation, or treating with antibodies directed against the interleukin-2 receptor, which for example bind to the a subunit of the interleukin-2 receptor on activated lymphocytes and result in prevention of interleukin-2-mediated responses, or with antibodies directed against CD40, CD40L, TNF-α or TNF α-receptor.

Treatment with corticosteroids is of course also contemplated, with however the disadvantage that the treatment results in an aspecific blockade of cytokine-gene transcription in various types of cells (lymphocytes, macrophages, and other antigen-presenting cells such as dendritic cells) that will counter the more specific activity of the gene-regulatory peptide as provided herein. Corticosteroid treatment should therefore be contemplated only on a case-by-case basis.

In a much preferred embodiment, the invention provides a method for modulating transplant survival in a recipient of the transplant comprising providing the transplant with a signaling molecule comprising a peptide, in particular a short, gene regulatory peptide as provided herein or a functional analogue thereof wherein the HLA-type of the transplant mismatches with the HLA-type of the recipient. Under those circumstances, the recipient will benefit most from the herein proposed treatment with the gene-regulatory peptide.

The invention is further explained with the use of the following illustrative examples.

EXAMPLES

The gene-regulatory activity of a gene-regulatory peptide, in particular of a NF-κB regulating peptide such as selected from the group of peptides LQG, AQG, LQGV (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), LQGVLPALPQVVC (SEQ ID NO: 17), LPGCPRGVNPVVS (SEQ ID NO: 18), LPGC (SEQ ID NO: 19), MTRV (SEQ ID NO: 20), MTR, VVC is manifested in the following way. Classically, many genes are regulated not by a signaling molecule that enters the cells but by molecules that bind to specific receptors on the surface of cells. Interaction between cell-surface receptors and their ligands can be followed by a cascade of intracellular events including variations in the intracellular levels of so-called second messengers (diacylglycerol, $Ca^{2+}$, cyclic nucleotides). The second messengers in turn lead to changes in protein phosphorylation through the action of cyclic AMP, cyclic GMP, calcium-activated protein kinases, or protein kinase C, which is activated by diaglycerol. Many of these classic responses to binding of ligands to cell-surface receptors are cytoplasmic and do not involve immediate gene activation in the nucleus. Some receptor-ligand interactions, however, are known to cause prompt nuclear transcriptional activation of a specific and limited set of genes. However, progress has been slow in determining exactly how such activation is achieved. In a few cases, the transcriptional proteins that respond to cell-surface signals have been characterized.

One of the clearest examples of activation of a pre-existing inactive transcription factor following a cell-surface interaction is the nuclear factor (NF)-κB, which was originally detected because it stimulates the transcription of genes encoding immunoglobulin light chains of the κ class in B-lymphocytes. The binding site for NK-κB in the κ gene is well defined (see for example P. A. Baeuerle and D. Baltimore, 1988, Science 242:540), providing an assay for the presence of the active factor. This factor exists in the cytoplasm of lymphocytes complexed with an inhibitor. Treatment of the isolated complex in vitro with mild denaturing conditions dissociates the complex, thus freeing NK-κB to bind to its DNA site. Release of active NF-κB in cells is now known to occur after a variety of stimuli including treating cells with bacterial lipopolysaccharide (LPS) and extracellular polypeptides as well as chemical molecules (e.g. phobol esters) that stimulate intracellular phosphokinases. Thus a phosphorylation event triggered by many possible stimuli may account for NF-κB conversion to the active state. The active factor is then translocated to the cell nucleus to stimulate transcription only of genes with a binding site for active NF-κB. We have found that a variety of short peptides as indicated above exert a modulatory activity on NF-κB activity.

Considering that the inflammatory response involves the sequential release of mediators and the recruitment of circulating leukocytes, which become activated at the inflammatory site and release further mediators (Nat. Med. 7:1294; 2001), we provided using NF-κB regulating peptide in the field of transplantation medicine, e.g., by providing pharmaceutical compositions and methods for use in the field of transplantation medicine. Considering that NF-κB is thought by many to be a primary effector of disease (A. S. Baldwin, J. Clin. Invest., 2001, 107:3-6), numerous efforts are underway to develop safe inhibitors of NF-κB to be used in treatment of both chronic and acute disease situations.

For example, the invention provides a method for perfusing a transplant with a perfusing fluid comprising at least one gene-regulatory peptide, preferably an NFκB down-regulating peptides as provided herein; ischemic or pre-implantation damage due to activation of NF-κB in the transplant can then be greatly diminished, allowing a wider use of the transplants. It is now provided that the use also allows reducing the risk on chronic transplant rejection, allowing increasing transplant survival. The invention provides a method for avoiding acute and in particular chronic rejection of a transplant and increasing transplant survival in a recipient of the transplant comprising providing the transplant with a gene-regulatory peptide or functional analogue thereof, herein also called a signalling molecule. It is preferred that the peptide is 3 to 15 amino acids long, more preferably, that the peptide is 3 to 9 amino acids long, it most preferred that the peptide is 4 to 6 amino acids long. It is in particular preferred that the signaling molecule is capable of inhibiting NF-κB/Rel protein activity. Functional analogue herein relates to the signaling molecular effect or activity as for example can be measured by measuring nuclear translocation of a relevant transcription factor, such as NF-κB in an NF-κB assay, or AP-1 in an AP-1 assay or by another method as provided herein. Fragments can be somewhat (i.e., 1 or 2 amino acids) smaller or larger on one or both sides, while still providing functional activity. In one embodiment of the invention, the peptide used as a signaling molecule a chemically modified peptide. A peptide modification includes phosphorylation (e.g. on a Tyr, Ser or Thr residue), N-terminal acetylation, C-terminal amidation, C-terminal hydrazide, C-terminal methyl ester, fatty acid attachment, sulfonation (tyrosine), N-terminal dansylation, N-terminal succinylation, tripalmitoyl-S-Glyceryl Cysteine (PAM3 Cys-OH) as well as farnesylation of a Cys residue. Systematic chemical modification of a peptide can for example be performed in the process of peptide optimization.

Synthetic peptides can be obtained using various procedures known in the art. These include solid phase peptide synthesis (SPPS) and solution phase organic synthesis (SPOS) technologies. SPPS is a quick and easy approach to synthesize peptides and small proteins. The C-terminal amino acid is typically attached to a cross-linked polystyrene resin via an acid labile bond with a linker molecule. This resin is insoluble in the solvents used for synthesis, making it relatively simple and fast to wash away excess reagents and by-products. The peptide, or its functional analogue, modification or derivative, can be administered as the entity as such or as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to sugars, lipids, other polypeptides, nucleic acids and PNA; and function in-situ as a conjugate or be released locally after reaching a targeted tissue or organ.

In response to a variety of pathophysiological and developmental signals, the NFκB/Rel family of transcription factors is activated and form different types of hetero- and homodimers among themselves to regulate the expression of target genes containing κB-specific binding sites. NF-κB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFκB is a heterodimer of p65 (RELA) and p50 (NF-κB1). Among the activated NFκB dimers, p50-p65 heterodimers are known to be involved in enhancing the transcription of target genes and p50-p50 homodimers in transcriptional repression. However, p65-p65 homodimers are known for both transcriptional activation and repressive activity against target genes. κB DNA binding sites with varied affinities to different NFB dimers have been discovered in the promoters of several eukaryotic genes and the balance between activated NFκB homo- and heterodimers ultimately determines the nature and level of gene expression within the cell. The term "NFκB-regulating peptide" as used herein refers to a peptide or functional analogue or a modification or derivative thereof capable of modulating the activation of members of the NFκB/Rel family of transcription factors. Examples of such peptides that are particularly useful in a method or composition according to the invention are selected from the group of VLPALPQVVC (SEQ ID NO: 21), LQGVLPALPQ (SEQ ID NO: 22), LQGV (SEQ ID NO: 1), AQGV (SEQ ID NO: 2), GVLPALPQ (SEQ ID NO: 23), VLPALP (SEQ ID NO: 4), VLPALPQ (SEQ ID NO: 13), GVLPALP (SEQ ID NO: 16), VVC, MTRV (SEQ ID NO: 20), and MTR. Modulation of the activation of NFκB can lead to enhanced transcription of target genes. Also, it can lead to transcriptional repression of target genes. NFκB activation can be regulated at multiple levels. For example, the dynamic shuttling of the inactive NFκB dimers between the cytoplasm and nucleus by IκB proteins and its termination by phosphorylation and proteasomal degradation, direct phosphorylation, acetylation of NFκB factors, and dynamic reorganization of NFκB subunits among the activated NFκB dimers have all been identified as key regulatory steps in NFκB activation and, consequently, in NFκB-mediated transcription processes. Thus, an NFκB-regulating peptide is capable of modulating the transcription of genes that are under the control of NFκB/Rel family of transcription factors. Modulating comprises the upregulation or the down regulation of transcription.

The term "pharmaceutical composition" as used herein is intended to cover both the active signaling molecule alone or a composition containing the signaling molecule together with a pharmaceutically acceptable carrier, diluent or excipient. Acceptable diluents of an oligopeptide as described herein in the detailed description are for example physiological salt solutions or phosphate buffered salt solutions. In a preferred embodiment, the invention provides use of a signaling molecule comprising a peptide or functional analogue thereof for the production of a pharmaceutical composition for the treatment of a transplant allowing modulating transplant survival in a recipient of the transplant. It is herein provided to produce a pharmaceutical composition wherein the signaling molecule modulates translocation and/or activity of a gene transcription factor. It is in particular useful to provide a pharmaceutical composition wherein the gene transcription factor comprises an NF-κB/Rel protein. For example, to counter ischemia-reperfusion damage of a transplant, for example derived from a brain dead donor or, to prevent ischemia-reperfusion damage during cold storage and transport of a transplant, it is herein recommended to provide a pharmaceutical composition by which translocation and/or activity of the NF-κB/Rel protein is inhibited. Such a composition can be a transplant preservation or perfusion fluid as described herein, comprising a gene-regulatory peptide or functional analogue thereof. It is useful to select the peptide from the group of peptides LQG, AQG, LQGV (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), LQGVLPALPQVVC (SEQ ID NO: 17), LPGCPRGVNPVVS (SEQ ID NO: 18), LPGC (SEQ ID NO: 19), MTRV (SEQ ID NO: 20), MTR, VVC, or functional analogues thereof, but other gene-regulatory peptides can also be selected. As described above, under certain circumstances it is preferred that the pharmaceutical composition is hypertonic. It may also be useful to add to the perfusion fluid an anticoagulant, such as heparin, or in conditions where disseminated intravascular coagulation (DIC) of the transplant is expected (such as with cadaveric donors) to add (recombinant) Activated Protein C to a perfusion fluid as herein provided. Where the Activated Protein C resolves the diffuse coagulation leading to ischemia, the NF-κB regulating peptide in the perfusion fluid helps reducing reperfusion damage. In most circumstances, the treatment with the preservation or perfusion fluid comprises providing the transplant with the signaling molecule after the transplant has been taken out of the donor. It is in particular useful to further treat the recipient with one of the above mentioned classically known pharmaceutical compositions for further reducing the risk of transplant rejection, especially in those cases wherein the HLA-type of the transplant mismatches with the HLA-type of the recipient.

The invention also provides a transplant preservation fluid or a transplant perfusion fluid comprising as a signaling molecule a peptide or functional analogue capable of modulating translocation and/or activity of a gene transcription factor.

In a specific embodiment, such a fluid also comprises (recombinant) Activated Protein C, especially when the gene transcription factor comprises an NF-κB/Rel protein, or the AP-1 protein. The peptides added to such a fluid, such as LQG, AQG, LQGV. (SEQ ID NO: 1), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), VVCNYRDVRFESIRLPGCPRGVNPV-VSYAVALSCQCAL (SEQ ID NO: 24), RPRCRPINAT- LAVEKEGCPVCITVNTTICAGYCPT (SEQ ID NO: 25), SKAPPPSLPSPSRLPGPS (SEQ ID NO: 26), LQGVLPALPQVVC (SEQ ID NO: 17), SIRLPGCPRGVNPVVS (SEQ ID NO: 27), LPGCPRGVNPVVS (SEQ ID NO: 18), LPGC (SEQ ID NO: 19), MTRV (SEQ ID NO: 20), MTR, and VVC and others are for example prepared by solid-phase synthesis Detailed description.

In response to a variety of pathophysiological and developmental signals, the NFκB/Rel family of transcription factors is activated and form different types of hetero- and homodimers among themselves to regulate the expression of target genes containing κB-specific binding sites. NF-κB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFκB is a heterodimer of p65 (RELA) and p50 (NF-κB1). Among the activated NFκB dimers, p50-p65 heterodimers are known to be involved in enhancing the transcription of target genes and p50-p50 homodimers in transcriptional repression. However, p65-p65 homodimers are known for both transcriptional activation and repressive activity against target genes. κB DNA binding sites with varied affinities to different NFB dimers have been discovered in the promoters of several eukaryotic genes and the balance between activated NFκB homo- and heterodimers ultimately determines the nature and level of gene expression within the cell. The term "NFκB-regulating peptide" as used herein refers to a peptide or a modification or derivative thereof capable of modulating the activation of members of the NFκB/Rel family of transcription factors. Activation of NFκB can gene-regulatory to enhanced transcription of target genes. Also, it can gene-regulatory to transcriptional repression of target genes. NFκB activation can be regulated at multiple levels. For example, the dynamic shuttling of the inactive NFκB dimers between the cytoplasm and nucleus by IκB proteins and its termination by phosphorylation and proteasomal degradation, direct phosphorylation, acetylation of NFκB factors, and dynamic reorganization of NFκB subunits among the activated NFκB dimers have all been identified as key regulatory steps in NFκB activation and, consequently, in NFκB-mediated transcription processes. Thus, an NFκB-regulating peptide is capable of modulating the transcription of genes that are under the control of NFκB/Rel family of transcription factors. Modulating comprises the upregulation or the downregulation of transcription. In a preferred embodiment, a peptide according to the invention, or a functional derivative or analogue thereof is used for the production of a pharmaceutical composition. Examples of useful NFκB down-regulating peptides to be included in such a pharmaceutical composition are VLPALPQVVC (SEQ ID NO: 21), LQGVLPALPQ (SEQ ID NO: 22), LQG, LQGV (SEQ ID NO: 1), GVLPALPQ (SEQ ID NO: 23), VLPALP (SEQ ID NO: 4), VVC, MTR and circular LQGVLPALPQVVC (SEQ ID NO: 17). More gene-regulating peptides and functional analogues can be found in a (bio)assay, such as an NFκB translocation assay as pro vided herein. Most prominent among NFκB down-regulating peptides are VLPALPQVVC (SEQ ID NO: 21), LQGVLPALPQ (SEQ ID NO: 22), LQG, LQGV (SEQ ID NO: 1), and VLPALP (SEQ ID NO: 4). These are also capable of reducing production of NO by a cell. It is herein also provided to use a composition that comprises at least two oligopeptides or functional analogues thereof, each capable of down-regulation NFκB, and thereby reducing production of NO and/or TNF-α by a cell, in particular wherein the at least two oligopeptides are selected from the group LQGV (SEQ ID NO: 1), AQGV (SEQ ID NO: 5) and VLPALP (SEQ ID NO: 4). Useful NFκB up-regulating peptides are VLPALPQ (SEQ ID NO: 13), GVLPALP (SEQ ID NO: 16) and MTRV (SEQ ID NO: 20). As indicated, more gene-regulatory peptides may be founds with an appropriate (bio)assay. A gene-regulatory peptide as used herein is preferably short. Preferably, such a peptide is 3 to 15 amino acids long, and capable of modulating the expression of a gene, such as a cytokine, in a cell. In a preferred embodiment, a peptide is a signaling molecule that is capable of traversing the plasma membrane of a cell or, in other words, a peptide that is membrane-permeable. More preferably, wherein the lead peptide is 3 to 9 amino acids long, most preferred wherein the lead peptide is 4 to 6 amino acids long.

Functional derivative or analogue herein relates to the signaling molecular effect or activity as for example can be measured by measuring nuclear translocation of a relevant transcription factor, such as NF-κB in an NF-κB assay, or AP-1 in an AP-1 assay, or by another method as provided herein. Fragments can be somewhat (i.e., 1 or 2 amino acids) smaller or larger on one or both sides, while still providing functional activity. Such a bioassay comprises an assay for obtaining information about the capacity or tendency of a peptide, or a modification thereof, to regulate expression of a gene. A scan with for example a 15-mer, or a 12-mer, or a 9-mer, or a 8-mer, or a 7-mer, or a 6-mer, or a 5-mer, or a 4-mer or a 3-mer peptides can yield valuable information on the linear stretch of amino acids that form an interaction site and allows identification of gene-regulatory peptides that have the capacity or tendency to regulate gene expression. Gene-regulatory peptides can be modified to modulate their capacity or tendency to regulate gene expression, which can be easily assayed in an in vitro bioassay such as a reporter assay. For example, some amino acid at some position can be replaced with another amino acid of similar or different properties. Alanine (Ala)-replacement scanning, involving a systematic replacement of each amino acid by an Ala residue, is a suitable approach to modify the amino acid composition of a gene-regulatory peptide when in a search for a signaling molecule capable of modulating gene expression. Of course, such replacement scanning or mapping can be undertaken with amino acids other than Ala as well, for example with D-amino acids. In one embodiment, a peptide derived from a naturally occurring polypeptide is identified as being capable of modulating gene expression of a gene in a cell. Subsequently, various synthetic Ala-mutants of this gene-regulatory peptide are produced. These Ala-mutants are screened for their enhanced or improved capacity to regulate expression of a gene compared to gene-regulatory polypeptide.

Furthermore, a gene-regulatory peptide, or a modification or analogue thereof, can be chemically synthesized using D- and/or L-stereoisomers. For example, a gene-regulatory peptide that is a retro-inverso of an oligopeptide of natural origin is produced. The concept of polypeptide retro-inversion (assemblage of a natural L-amino acid-containing parent sequence in reverse order using D-amino acids) has been applied successfully to synthetic peptides. Retro-inverso modification of peptide bonds has evolved into a widely used peptidomimetic approach for the design of novel bioactive molecules which has been applied to many families of biologically active peptide. The sequence, amino acid composition and length of a peptide will influence whether correct assembly and purification are feasible. These factors also determine the solubility of the final product. The purity of a crude peptide typically decreases as the length increases. The yield of peptide for sequences less than 15 residues is usually satisfactory, and such peptides can typically be made without difficulty. The overall amino acid composition of a peptide is an important design variable. A peptide's solubility is strongly influenced by composition. Peptides with a high content of hydrophobic residues, such as Leu, Val, Ile, Met, Phe and Trp, will either have limited solubility in aqueous solution or be completely insoluble. Under these conditions, it can be difficult to use the peptide in experiments, and it may be difficult to purify the peptide if necessary. To achieve a good solubility, it is advisable to keep the hydrophobic amino acid content below 50% and to make sure that there is at least one charged residue for every five amino acids. At physiological pH Asp, Glu, Lys, and Arg all have charged side chains. A single conservative replacement, such as replacing Ala with Gly, or adding a set of polar residues to the N- or C-terminus, may also improve solubility. Peptides containing multiple Cys, Met, or Trp residues can also be difficult to obtain in high purity partly because these residues are susceptible to oxidation and/or side reactions. If possible, one should choose sequences to minimize these residues. Alternatively, conservative replacements can be made for some residues. For instance, norleucine can be used as a replacement for Met, and Ser is sometimes used as a less reactive replacement for Cys. If a number of sequential or overlapping peptides from a protein sequence are to be made, making a change in the starting point of each peptide may create a better balance between hydrophilic and hydrophobic residues. A change in the number of Cys, Met, and Trp residues contained in individual peptides may produce a similar effect. In another embodiment of the invention, a gene-regulatory peptide capable of modulating gene expression is a chemically modified peptide. A peptide modification includes phosphorylation (e.g., on a Tyr, Ser or Thr residue), N-terminal acetylation, C-terminal amidation, C-terminal hydrazide, C-terminal methyl ester, fatty acid attachment, sulfonation (tyrosine), N-terminal dansylation, N-terminal succinylation, tripalmitoyl-S-Glyceryl Cysteine (PAM3 Cys-OH) as well as farnesylation of a Cys residue. Systematic chemical modification of a gene-regulatory peptide can for example be performed in the process of gene-regulatory peptide optimization.

Synthetic peptides can be obtained using various procedures known in the art. These include solid phase peptide synthesis (SPPS) and solution phase organic synthesis (SPOS) technologies. SPPS is a quick and easy approach to synthesize peptides and small proteins. The C-terminal amino acid is typically attached to a cross-linked polystyrene resin via an acid labile bond with a linker molecule. This resin is insoluble in the solvents used for synthesis, making it relatively simple and fast to wash away excess reagents and by-products.

The peptides as mentioned in this document such as LQG, AQG, LQGV (SEQ ID NO: 1 of the hereby incorporated accompanying SEQUENCE LISTING), AQGV (SEQ ID NO: 2), LQGA (SEQ ID NO: 3), VLPALP (SEQ ID NO: 4), ALPALP (SEQ ID NO: 5), VAPALP (SEQ ID NO: 6), ALPALPQ (SEQ ID NO: 7), VLPAAPQ (SEQ ID NO: 8), VLPALAQ (SEQ ID NO: 9), LAGV (SEQ ID NO: 10), VLAALP (SEQ ID NO: 11), VLPALA (SEQ ID NO: 12), VLPALPQ (SEQ ID NO: 13), VLAALPQ (SEQ ID NO: 14), VLPALPA (SEQ ID NO: 15), GVLPALP (SEQ ID NO: 16), VVCNYRDVRFESIRLPGCPRGVNPV-VSYAVALSCQCAL (SEQ ID NO: 24), RPRCRPINAT-LAVEKEGCPVCITVNTTICAGYCPT (SEQ ID NO: 25), SKAPPPSLPSPSRLPGPS (SEQ ID NO: 26), LQGVL-PALPQVVC (SEQ ID NO: 17), SIRLPGCPRGVNPVVS (SEQ ID NO: 27), LPGCPRGVNPVVS (SEQ ID NO: 18), LPGC (SEQ ID NO: 19), MTRV (SEQ ID NO: 20), MTR, and VVC were prepared by solid-phase synthesis using the fluorenylmethoxycarbonyl (Fmoc)/tert-butyl-based methodology with 2-chlorotrityl chloride resin as the solid support. The side-chain of glutamine was protected with a trityl function. The peptides were synthesized manually. Each coupling consisted of the following steps: (i) removal of the α-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/ diisopropylethylamine (DIEA) in DMF/NMP. Upon completion of the synthesis, the peptide resin was treated with a mixture of trifluoroacetic acid (TFA)/$H_2O$/triisopropylsilane (TIS) 95:2.5:2.5. After 30 minutes TIS was added until decolorization. The solution was evaporated in vacuo and the peptide precipitated with diethyl ether. The crude peptides were dissolved in water (50-100 mg/ml) and purified by reverse-phase high-performance liquid chromatography (RP-HPLC). HPLC conditions were: column: Vydac TP21810C18 (10× 250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For example for peptides LQG and LQGV (SEQ ID NO: 1): 10 minutes 100% A followed by linear gradient 0-10% B in 50 minutes. For example for peptides VLPALP (SEQ ID NO: 4) and VLPALPQ (SEQ ID NO: 13): 5 minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilised in 28 hours. Peptides later were prepared for use by dissolving them in PBS.

RAW 264.7 macrophages, obtained from American Type Culture Collection (Manassas, Va.), were cultured at 37° C. in 5% CO2 using DMEM containing 10% FBS and antibiotics (100 μ/ml of penicillin, and 100 μg/ml streptomycin). Cells ($1 \times 10^6$/ml) were incubated with peptide (10 μg/ml) in a volume of 2 ml. After 8 h of cultures cells were washed and prepared for nuclear extracts.

Nuclear extracts and EMSA were prepared according to Schreiber et al. Methods (Schrieber et al. 1989, Nucleic Acids Research 17). Briefly, nuclear extracts from peptide stimulated or nonstimulated macrophages were prepared by cell lysis followed by nuclear lysis. Cells were then suspended in 400 μl of buffer (10 mM HEPES (pH 7.9), 10 mM KCl, 0.1 mM KCL, 0.1 mM EDTA, 0.1 mM EGTA, 1 mM DTT, 0.5 mM PMSF and protease inhibitors), vigorously vortexed for 15 s, left standing at 4° C. for 15 min, and centrifuged at 15,000 rpm for 2 min. The pelleted nuclei were resuspended in buffer (20 mM HEPES (pH 7.9), 10% glycerol, 400 mM NaCl, 1 mM EDTA, 1 mM EGTA, 1 mM DTT, 0.5 mM PMSF and protease inhibitors) for 30 min on ice, then the lysates were centrifuged at 15,000 rpm for 2 min. The supernatants containing the solubilized nuclear proteins were stored at −70° C. until used for the Electrophoretic Mobility Shift Assays (EMSA).

Electrophoretic mobility shift assays were performed by incubating nuclear extracts prepared from control (RAW 264.7) and peptide treated RAW 264.7 cells with a 32P-labeled double-stranded probe (5' AGCTCAGAGGGG-GACTTTCCGAGAG 3') (SEQ ID NO: 28) synthesized to represent the NF-κB binding sequence. Shortly, the probe was end-labeled with T4 polynucleotide kinase according to manufacturer's instructions (Promega, Madison, Wis.). The annealed probe was incubated with nuclear extract as follows:

in EMSA, binding reaction mixtures (20 µl) contained 0.25 µg of poly(dI-dC) (Amersham Pharmacia Biotech) and 20,000 rpm of 32P-labeled DNA probe in binding buffer consisting of 5 mM EDTA, 20% Ficoll, 5 mM DTT, 300 mM KCl and 50 mM HEPES. The binding reaction was started by the addition of cell extracts (10 µg) and was continued for 30 min at room temperature. The DNA-protein complex was resolved from free oligonucleotide by electrophoresis in a 6% polyacrylamide gel. The gels were dried and exposed to x-ray films.

The transcription factor NF-κB participates in the transcriptional regulation of a variety of genes. Nuclear protein extracts were prepared from LPS and peptide treated RAW264.7 cells or from LPS treated RAW264.7 cells. In order to determine whether the peptide modulates the translocation of NF-κB into the nucleus, on these extracts EMSA was performed. Here we see that indeed peptides are able to modulate the translocation of NF-κB since the amount of labeled oligonucleotide for NF-κB is reduced. In this experiment peptides that show the modulation of translocation of NF-κB are: VLPALPQVVC (SEQ ID NO: 21), LQGVLPALPQ (SEQ ID NO: 22), LQG, LQGV (SEQ ID NO: 1), GVLPALPQ (SEQ ID NO: 23), VLPALP (SEQ ID NO: 4), VLPALPQ (SEQ ID NO: 13), GVLPALP (SEQ ID NO: 16), VVC, MTRV (SEQ ID NO: 20), MTR.

RAW 264.7 mouse macrophages were cultured in DMEM, containing 10% or 2% FBS, penicillin, streptomycin and glutamine, at 37° C., 5% $CO_2$. Cells were seeded in a 12-wells plate ($3\times10^6$ cells/ml) in a total volume of 1 ml for 2 hours and then stimulated with LPS (*E. coli* 026:B6; Difco Laboratories, Detroit, Mich., USA) and/or gene-regulatory peptide (1 microgr/ml). After 30 minutes of incubation plates were centrifuged and cells were collected for nuclear extracts. Nuclear extracts and EMSA were prepared according to Schreiber et al. Cells were collected in a tube and centrifuged for 5 minutes at 2000 rpm (rounds per minute) at 4° C. (Universal 30 RF, Hettich Zentrifuges). The pellet was washed with ice-cold Tris buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty five micro liter 10% NP-40 was added and the sample was centrifuged (2 minutes, 4000 rpm, 4° C.). The supernatant (cytoplasmic fraction) was collected and stored at −70° C. The pellet, which contains the nuclei, was washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples were left to shake at 4° C. for at least 60 minutes. Finally the samples were centrifuged and the supernatant (nucleic fraction) was stored at −70° C.

Bradford reagent (Sigma) was used to determine the final protein concentration in the extracts. For electrophoretic mobility shift assays an oligonucleotide representing NF-κB binding sequence (5'-AGC TCA GAG GGG GAC TTT CCG AGA G-3') (SEQ ID NO: 28) was synthesized. Hundred pico mol sense and antisense oligo were annealed and labeled with γ-32P-dATP using T4 polynucleotide kinase according to manufacture's instructions (Promega, Madison, Wis.). Nuclear extract (5-7.5 µg) was incubated for 30 minutes with 75000 cpm probe in binding reaction mixture (20 microliter) containing 0.5 µg poly dI-dC (Amersham Pharmacia Biotech) and binding buffer BSB (25 mM $MgCl_2$, 5 mM $CaCl_2$, 5 mM DTT and 20% Ficoll) at room temperature. The DNA-protein complex was resolved from free oligonucleotide by electrophoresis in a 4-6% polyacrylamide gel (150 V, 2-4 hours). The gel was then dried and exposed to x-ray film. The transcription factor NF-κB participates in the transcriptional regulation of a variety of genes. Nuclear protein extracts were prepared from either LPS (1 mg/ml), peptide (1 mg/ml) or LPS in combination with peptide treated and untreated RAW264.7 cells. In order to determine whether the peptides modulate the translocation of NF-κB into the nucleus, on these extracts EMSA was performed. Peptides are able to modulate the basal as well as LPS induced levels of NF-κB. In this experiment peptides that show the inhibition of LPS induced translocation of NF-κB are: VLPALPQVVC (SEQ ID NO: 21), LQGVLPALPQ (SEQ ID NO: 22), LQG, LQGV (SEQ ID NO: 1), GVLPALPQ (SEQ ID NO: 23), VLPALP (SEQ ID NO: 4), VVC, MTR and circular LQGVLPALPQVVC (SEQ ID NO: 17). Peptides that in this experiment promote LPS induced translocation of NF-κB are: VLPALPQ (SEQ ID NO: 13), GVLPALP (SEQ ID NO: 16) and MTRV (SEQ ID NO: 20). Basal levels of NF-κB in the nucleus was decreased by VLPALPQVVC (SEQ ID NO: 21), LQGVLPALPQ (SEQ ID NO: 22), LQG and LQGV (SEQ ID NO: 1) while basal levels of NF-κB in the nucleus was increased by GVLPALPQ (SEQ ID NO: 23), VLPALPQ (SEQ ID NO: 7), GVLPALP (SEQ ID NO: 16), VVC, MTRV (SEQ ID NO: 20), MTR and LQGVLPALPQVVC (SEQ ID NO: 17). In other experiments, QVVC (SEQ ID NO: 29) also showed the modulation of translocation of NF-κB into nucleus (data not shown).

Further modes of identification of gene-regulatory peptides by NFκB analysis:

Cells: Cells will be cultured in appropriate culture medium at 37° C., 5% $CO_2$. Cells will be seeded in a 12-wells plate (usually $1\times10^6$ cells/ml) in a total volume of 1 ml for 2 hours and then stimulated with regulatory peptide in the presence or absence of additional stimuli such as LPS. After 30 minutes of incubation plates will be centrifuged and cells are collected for cytosolic or nuclear extracts.

Nuclear Extracts: Nuclear extracts and EMSA could be prepared according to Schreiber et al. Method (Schriber et al. 1989, Nucleic Acids Research 17). Cells are collected in a tube and centrifuged for 5 minutes at 2000 rpm (rounds per minute) at 4° C. (Universal 30 RF, Hettich Zentrifuges). The pellet is washed with ice-cold Tris buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty five micro liter 10% NP-40 is added and the sample is centrifuged (2 minutes, 4000 rpm, 4° C.). The supernatant (cytoplasmic fraction) was collected and stored at −70° C. for analysis. The pellet, which contains the nuclei, is washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples are left to shake at 4° C. for at least 60 minutes. Finally the samples are centrifuged and the supernatant (nucleic fraction) is stored at −70° C. for analysis.

Bradford reagent (Sigma) could be used to determine the final protein concentration in the extracts.

EMSA: For Electrophoretic mobility shift assays an oligonucleotide representing NF-κB binding sequence such as (5'-AGC TCA GAG GGG GAC TTT CCG AGA G-3') (SEQ ID NO: 28) are synthesized. Hundred pico mol sense and antisense oligo are annealed and labeled with γ-$^{32}$P-dATP using T4 polynucleotide kinase according to manufacture's instructions (Promega, Madison, Wis.). Cytosolic extract or nuclear extract (5-7.5 µg) from cells treated with regulatory peptide or from untreated cells is incubated for 30 minutes with 75000 cpm probe in binding reaction mixture (20 □l) containing 0.5 µg poly dI-dC (Amersham Pharmacia Biotech) and binding buffer BSB (25 mM $MgCl_2$, 5 mM $CaCl_2$, 5 mM DTT and 20% Ficoll) at room temperature. Or cytosolic and nuclear extract from untreated cells or from cells treated with stimuli could also be incubated with probe in binding reaction mixture and binding buffer. The DNA-protein complexes are resolved from free oligonucleotide by electrophoresis in a 4-6% polyacrylamide gel (150 V, 2-4 hours). The gel is then dried and exposed to x-ray film. Peptides can be biotinylated and incubated with cells. Cells are then washed with phosphate-buffered saline, harvested in the absence or presence of certain stimulus (LPS, PHA, TPA, anti-CD3, VEGF, TSST-1, VIP or know drugs etc.). After culturing cells are lysed and cells lysates (whole lysate, cytosolic fraction or nuclear fraction) containing 200 micro gram of protein are incubated with 50 miroliter Neutr-Avidin-plus beads for 1 h at 4° C. with constant shaking. Beads are washed five times with lysis buffer by centrifugation at 6000 rpm for 1 min. Proteins are eluted by incubating the beads in 0.05 N NaOH for 1 min at room temperature to hydrolyze the protein-peptide linkage and analyzed by SDS-polyacrylamide gel electrophoresis followed by immunoprecipitated with agarose-conjugated anti-NF-κB subunits antibody or immunoprecipitated with antibody against to the studied target. After hydrolyzing the protein-peptide linkage, the sample could be analyzed on HPLS and mass-spectrometry. Purified NF-κB subunits or cell lysate interaction with biotinylated regulatory peptide can be analyzed on biosensor technology. Peptides can be labeled with FITC and incubated with cells in the absence or presence of different stimulus. After culturing, cells can be analyzed with fluorescent microscopy, confocal microscopy, flow cytometry (cell membrane staining and/or intracellular staining) or cells lysates are made and analyzed on HPLC and mass-spectrometry. NF-κB transfected (reporter gene assay) cells and gene array technology can be used to determine the regulatory effects of peptides.

HPLC and mass-spectrometry analysis: Purified NF-κB subunit or cytosolic/nuclear extract is incubated in the absence or presence of (regulatory) peptide is diluted (2:1) with 8 N guanidinium chloride and 0.1% trifluoroacetic acid, injected into a reverse-phase HPLC column (Vydac C18) equilibrated with solvent A (0.1% trifluoroacetic acid), and eluted with a gradient of 0 to 100% eluant B (90% acetonitrile in solvent A). Factions containing NF-κB subunit are pooled and concentrated. Fractions are then dissolved in appropriate volume and could be analyzed on mass-spectrometry.

TABLE 1

An example of an improved perfusion fluid

| Components | Concentration (mM) |
|---|---|
| Na-gluconate | 80 |
| KH2PO4 | 25 |
| Glucose | 10 |
| Glutathione | 3 |
| Mg-gluconate | 5 |
| HEPES-buffer | 10 |
| CaCl2 | 0.5 |
| Adenosine (or adenine and ribose) | 5 |
| NF-κB regulating peptide (mg/l) | 1-1000 |
| Insulin (iu/l) | 80 |
| Penicillin (iu/l) | 200.000 |
| Mannitol | 20 |
| Hydroxyethyl starch (g/l) | 50 |

Some Final Concentrations:

Na+=135-140 mM; K+=25 mM; pH=7.35 (added NaOH); mOsm/l=330-350

Further References:

It was thought before that breakdown products of hCG were involved in immuno-modulation (PCT International Publications WO99/59671 and WO01/72831) or in the treatment of wasting syndrome, cancer (PCT International Publications WO97/49721, WO01/10907, and WO01/11048) but a relationship with modulation of gene expression was not forwarded in these publications.

In Table 2, the effect of ALA-replacement (PEPSCAN) in peptide LQGV (SEQ ID NO: 1) in septic shock experiments is shown. In Table 3, the results of additional shock experiments with AQGV (SEQ ID NO:2) are shown. Table 4 illustrates additional results of the same experiments. Table 5 illustrates a summary of different experiments with AQGV (SEQ ID NO:2). Table 6 illustrates modulation of NO and/or TNF-α with AQGV (SEQ ID NO:2). NO production is a central mediator of the vascular and inflammatory response. Results show that macrophages (RAW 264.7) stimulated with LPS produce large amounts of NO. However, these cells co-stimulated with AQGV (SEQ ID NO:2), even in a very low dose (1 pg/ml), inhibited the production of NO. Further details on the experiments relating to Tables 2-6 may be found in the disclosure of U.S. application Ser. No. 10/028,075, filed Dec. 21, 2001.

TABLE 2

Additional results of shock experiments

| SEQUENCE ID: | ANTI-SHOCK EFFECT |
|---|---|
| LQGV (SEQ ID NO:1) | +++ |
| AQGV (SEQ ID NO:2) | +++ |

TABLE 3

Further additional results of shock experiments

| | % SURVIVAL IN TIME (HRS) | | | |
|---|---|---|---|---|
| PEPTIDES | Tx 0 | 14 | Tx 24 | 48 |
| PBS | 100 | 100 | 100 | 0 |
| AQGV (SEQ ID NO:2) | 100 | 100 | 100 | 100 |

TABLE 4

Further additional results

| | SICKNESS SCORES | | | |
|---|---|---|---|---|
| PEPTIDES | Tx 0 | 14 | Tx 24 | 48 |
| PBS | 0,0,0,0,0,0 | 5,5,5,5,4,4 | 5,5,5,5,5,5 | ††††††  |
| AQGV (SEQ ID NO:2) | 0,0,0,0,0,0 | 1,1,2,2,3,3 | 1,1,2,2,2,2 | 1,1,1,1,1,1 |

TABLE 5

Summary of results of AQGV (SEQ ID NO:2) in various experiments.

| SEQUENCE | SEPSIS | ANGIOGENSIS | CAO | DC | NOD |
|---|---|---|---|---|---|
| AQGV (SEQ ID NO:2) | + | + | | + | |

+ = effects; −+ = variable effect; no entry is no effect or not yet tested when table was assembled

TABLE 6

Modulation of NO and/or TNF-α.

| MODULATION OF NO AND/OR TNF-α SEQUENCE | TNF-A | NO | TNF-A and NO |
|---|---|---|---|
| AQGV (SEQ ID NO:2) | ++++ | ++++ | +++++++ | from −+ to +++++++ indicates from barely active to very active in modulating

---

What is claimed is:

1. A method for improving transplant survival in a recipient of a transplant, said method comprising providing the transplant with a compound comprising an isolated peptide consisting of AQGV (SEQ ID NO:2), wherein damage caused by an ischemic event in the transplant is reduced, wherein the ischemic event is a renal ischemic-reperfusion injury.

2. The method according to claim 1 comprising providing the donor of said transplant with said compound.

3. The method according to claim 1 comprising providing said transplant with said compound after the transplant has been removed from the transplant's donor.

4. The method according to claim 1 further comprising treating said recipient with a pharmaceutical composition, other than said compound, for reducing the risk of transplant rejection.

5. The method according to claim 1 wherein the HLA-type of the transplant mismatches with the HLA-type of the recipient.

* * * * *

UNITED STATES PATENT AND TRADEMARK OFFICE
CERTIFICATE OF CORRECTION

PATENT NO. : 7,501,391 B2
APPLICATION NO. : 10/409027
DATED : March 10, 2009
INVENTOR(S) : Nisar Ahmed Khan et al.

It is certified that error appears in the above-identified patent and that said Letters Patent is hereby corrected as shown below:

On the title page:
In ITEM (56) References Cited
    FOREIGN PATENT DOCUMENTS    Add entry --EP    1 138 692 A1    10/2001--

Signed and Sealed this
Nineteenth Day of February, 2013

Teresa Stanek Rea
*Acting Director of the United States Patent and Trademark Office*